United States Patent
Furuki et al.

(10) Patent No.: US 6,681,624 B2
(45) Date of Patent: Jan. 27, 2004

(54) THERMAL FLOWMETER WITH FLUID DESCRIMINANT FUNCTION

(75) Inventors: Shinya Furuki, Ageo (JP); Kiyoshi Yamagishi, Ageo (JP)

(73) Assignee: Mitsui Mining & Smelting Co., Ltd., Tokyo (JP)

( * ) Notice: Subject to any disclaimer, the term of this patent is extended or adjusted under 35 U.S.C. 154(b) by 0 days.

(21) Appl. No.: 10/149,867

(22) PCT Filed: Dec. 6, 2000

(86) PCT No.: PCT/JP00/08622
§ 371 (c)(1),
(2), (4) Date: Oct. 15, 2002

(87) PCT Pub. No.: WO01/44761
PCT Pub. Date: Jun. 21, 2001

(65) Prior Publication Data
US 2003/0056585 A1 Mar. 27, 2003

(30) Foreign Application Priority Data
Dec. 15, 1999 (JP) .............................. 11-356074

(51) Int. Cl.⁷ ................................................ G01F 1/68
(52) U.S. Cl. .................................................. 73/204.13
(58) Field of Search ....................... 73/204, 204.13, 73/204.17, 204.23

(56) References Cited

U.S. PATENT DOCUMENTS

| | | | | |
|---|---|---|---|---|
| 4,480,467 A | * | 11/1984 | Harter et al. | 73/204.15 |
| 4,491,024 A | * | 1/1985 | Miller, Jr. | 73/861.95 |
| 5,119,674 A | * | 6/1992 | Nielsen | 73/204.24 |
| 5,525,040 A | * | 6/1996 | Andreae et al. | 417/32 |
| 5,629,481 A | * | 5/1997 | Sultan | 73/204.18 |
| 5,672,258 A | * | 9/1997 | Greenblatt et al. | 204/430 |

FOREIGN PATENT DOCUMENTS

| | | |
|---|---|---|
| JP | 11-118570 | 4/1999 |
| WO | WO 99/19694 | 4/1999 |

* cited by examiner

Primary Examiner—Edward Lefkowitz
Assistant Examiner—Jewel V. Thompson
(74) Attorney, Agent, or Firm—Frommer Lawrence & Haug LLP; Ronald R. Santucci

(57) ABSTRACT

A thermal flowmeter is provided with a flow rate detecting unit (4) containing a heating element, a flow rate detecting temperature sensing element and a flow rate detecting electroconductive fin plate (44) extending into a fluid flow passage (3), which are disposed so as to enable heat transfer therebetween, the flow rate detecting temperature sensing element varying in electrical characteristic value in accordance with the flow of the fluid in the fluid flow passage (3); and, a fluid temperature detecting unit (6) containing a fluid temperature detecting temperature sensing element and a fluid temperature detecting electroconductive fin plate (44') extending into the fluid flow passage (3), which are disposed so as to enable heat transfer therebetween, the fluid temperature detecting temperature sensing element varying in electrical characteristic value in accordance with the temperature of the fluid. The flow rate of the fluid is detected on the basis of the electrical characteristic values of the flow rate detecting and fluid temperature detecting temperature sensing elements, and a fluid discrimination is effected by determining a conductivity between the flow rate detecting and fluid temperature detecting fin plates (44, 44'). According to this thermal flowmeter, with simple constitution, discrimination of whether the fluid is the required one or not is effected so that passage of erroneous fluid can be avoided.

7 Claims, 4 Drawing Sheets

THERMAL FLOWMETER WITH FLUID DESCRIMINANT FUNCTION

This application is a 371 of PCT/JP00/08622 filed on Dec. 6, 2000, now WO 01/44761 A1 published Jun. 21, 2001, and claims priority benefits of Japanese patent application, 11-356074 filed Dec. 15, 1999.

TECHNICAL FIELD

The present invention relates to a fluid flow rate detecting technique, and particularly to a thermal flowmeter having a fluid discriminate function.

BACKGROUND TECHNIQUE

Various types have been known for a flowmeter [flow rate sensor] (or current meter [flow velocity sensor]) for measuring or detecting the flow rate (or flow velocity) of various kinds of fluid, particularly liquid. Of these types of flowmeters, a so-called thermal type (particularly, indirectly heated type) flowmeter has been used because the price thereof is lower.

One of indirectly heated type flowmeters is designed and used so that a sensor chip comprising a thin-film heating element and a thin-film temperature sensing element which are laminated on a substrate through an insulating layer by using the thin film technique is disposed so as to enable the heat transfer between the sensor chip and fluid flowing in a pipe. The electrical characteristic of the temperature sensing element, for example, the value of the electrical resistance is varied by supplying current to the heating element to heat the temperature sensing element. The variation of the electrical resistance value (based on increase of the temperature of the temperature sensing element) is varied in accordance with the flow rate (flow velocity) of the fluid flowing in the pipe. This is because a part of the heating value of the heating element is transferred into the fluid, the heating value thus diffused into the fluid is varied in accordance with the flow rate (flow velocity), and the heating value supplied to the temperature sensing element is varied in accordance with the variation of the heating value diffused into the fluid, so that the electrical resistance value of the temperature sensing element is varied. The variation of the electrical resistance value of the temperature sensing element is also varied in accordance with the temperature of the fluid. Therefore, a temperature sensing element for temperature compensation is installed in an electrical circuit for measuring or detecting the variation of the electrical resistance value of the temperature sensing element to reduce the variation of the flow rate measurement value due to the temperature of the fluid as much as possible.

With respect to the indirectly heated type flowmeter using the thin-film element as described above, JP(A)-11-118566 discloses an example of the indirectly heated type flowmeter. The flowmeter disclosed in this publication uses an electrical circuit (detection circuit) containing a bridge circuit to achieve the electrical output corresponding to a flow rate of the fluid.

In such a flowmeter, a value of the output of the detection circuit varies in accordance with thermal property of the fluid, even if actual flow rate value is equal. Therefore, in general, assuming that the fluid to be subjected to the flow rate detection is a required one, a calibration curve for the required fluid is used to convert the output value of the detection circuit to the flow rate value.

Recently, using an itemized fluid source obtained by dividing the same kind of fluid to be subjected to the flow rate detection, the flow rate is detected one by one for a plurality of itemized fluid sources.

For example, in synthesis of reagent of high degree of purity, synthesis of medicine, chemical analysis or the like, a small portable vessel containing a raw material fluid or a reagent fluid is connected to a reactor or an analyzer through a fluid flow passage, and the raw material fluid or the reagent fluid is fed to the reactor or the analyzer, while the flow rate of the fluid is detected at the fluid flow passage. When supplementing the raw material fluid or the reagent fluid, a vacant small portable vessel is replaced with a fresh small portable vessel filled with the raw material fluid or the reagent fluid to be connected to the reactor or the analyzer.

Furthermore, when a medical fluid is injected into a living body, the medical fluid is itemized so as to be filled up in portable medical fluid packs. A portable medical fluid pack is connected to the living body, for example a blood vessel thereof, through a fluid flow passage, and the medical fluid is injected into the living body, while the flow rate of the medical fluid is detected at the fluid flow passage. When supplementing the medical fluid, a vacant portable medical fluid pack is replaced with a fresh portable medical fluid pack filled with the medical fluid to be connected to the living body.

Utilization of the above itemized fluid source practically provides great advantage, however, there is a possibility of causing a mistake that a vacant itemized fluid source is replaced with a fresh itemized fluid source filled with non-required fluid when exchanging the itemized fluid source. In such a case, when the fluid is fed through the fluid flow passage, accurate flow rate detection cannot be conducted due to the difference in thermal property between the required fluid and the actually fed non-required fluid, and furthermore the incorrect fluid feeding causes an inferiority or accident in manufacturing or analysis or a medical accident.

Therefore, the present invention has an object to provide a thermal flowmeter having a function of discriminating whether the fluid to be subjected to the flow rate detection is the required one or not with simple constitution, in order to avoid the above-mentioned incorrect fluid flowing.

SUMMARY OF THE INVENTION

In order to attain the above objects, according to the present invention, there is provided a flowmeter, comprising:

a flow rate detecting unit containing a heating element, a flow rate detecting temperature sensing element and a flow rate detecting electroconductive heat transfer member extending into a fluid flow passage, which are disposed so as to enable heat transfer therebetween, the flow rate detecting temperature sensing element varying in electrical characteristic value in accordance with flow of a fluid in the fluid flow passage through heat exchange with the fluid in the fluid flow passage which is carried out through the flow rate detecting electroconductive heat transfer member; and a fluid temperature detecting unit containing a fluid temperature detecting temperature sensing element and a fluid temperature detecting electroconductive heat transfer member extending into the fluid flow passage, which are disposed so as to enable heat transfer therebetween, the fluid temperature detecting temperature sensing element varying in electrical characteristic value in accordance with the temperature of the fluid through heat exchange with the fluid in the fluid flow passage, wherein a flow rate of the fluid is detected on the basis of the electrical characteristic value of the flow rate detecting temperature sensing element and the electrical characteristic value of the fluid temperature detecting temperature sensing element, and fluid discrimination is effected by determining a conductivity between the flow rate detecting electroconductive heat transfer member and the fluid temperature detecting electroconductive heat transfer member.

In an aspect of the present invention, the fluid discrimination is effected by judging the fluid as a required one in case that a detected value of current flowing between the flow rate detecting electroconductive heat transfer member and the fluid temperature detecting electroconductive heat transfer member therethrough is a value within a predetermined range for the required fluid, while judging the fluid as not the required one in case that the detected value of current is a value without the predetermined range for the required fluid.

In an aspect of the present invention, the flow rate of the fluid is detected on the basis of an output of a detection circuit containing the flow rate detecting temperature sensing element and the fluid temperature detecting temperature sensing element and a calibration curve.

In an aspect of the present invention, a portion of the flow rate detecting electroconductive heat transfer member constitutes an electrode terminal of the flow rate detecting unit, and a portion of the fluid temperature detecting electroconductive heat transfer member constitutes an electrode terminal of the fluid temperature detecting unit.

DETAILED DESCRIPTION OF THE PREFERRED EMBODIMENTS

Preferred embodiments according to the present invention will be described hereunder with reference to the accompanying drawings.

Figure 1:
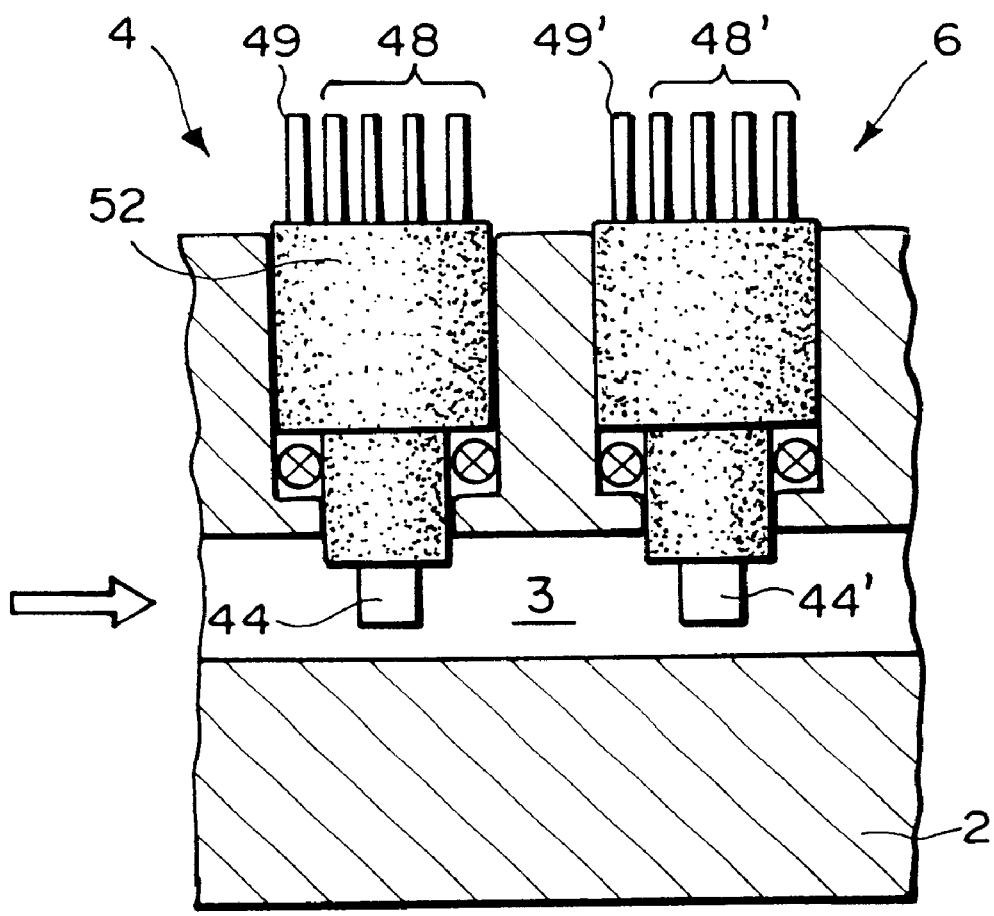
FIG. 1 is a schematic, partial cross-sectional view showing an embodiment of a flowmeter according to the present invention.

FIG. 1 is a schematic, partial cross-sectional view showing an embodiment of a flowmeter according to the present invention. As shown in FIG. 1, a fluid flow passage 3 is formed in a casing member 2. The casing member 2 is made of synthetic resin such as epoxy resin or polyphenylene sulfide resin or of metal. In case of metal casing member, it is preferable to form an insulating film on the inner surface thereof which determines the fluid flow passage 3. A flow rate detecting unit 4 and a fluid temperature detecting unit 6 are attached to the casing member 2 so as to confront the fluid flow passage 3.

Fluid flows in the direction of arrow in the fluid flow passage 3. That is, the casing member 2 has a fluid flow-in port (not shown) formed at a left-side end in FIG. 1 so as to communicate to the fluid flow passage 3, and a fluid source side pipe line is connected to the fluid flow in port. The casing member 2 also has a fluid flow-out port (not shown) formed at a right-side end in FIG. 1 so as to communicate to the fluid flow passage 3, and a fluid demand side pipe line is connected to the fluid flow-out port.

Figure 2:
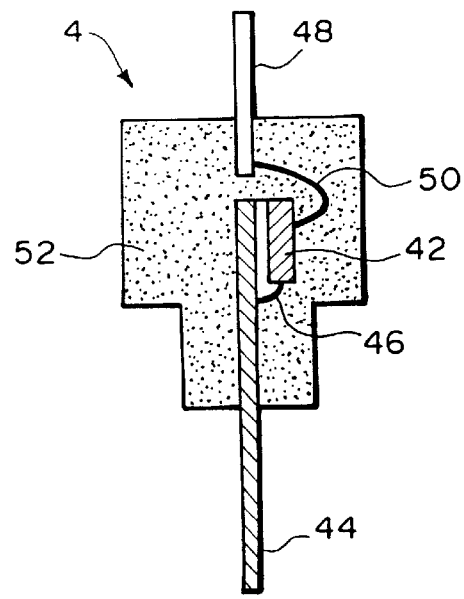
FIG. 2 is a cross-sectional view of a flow rate detecting unit.
Figure 3:
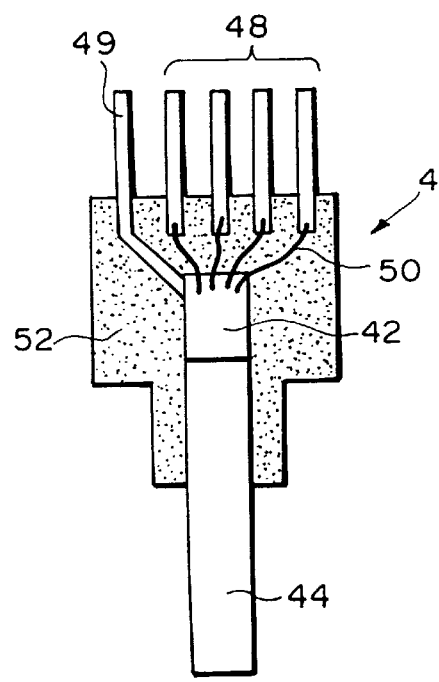
FIG. 3 is a cross-sectional view of a flow rate detecting unit.

FIGS. 2 and 3 are cross-sectional views of the flow rate detecting unit 4. In the flow rate detecting unit 4, a flow rate detector 42 is joined to the surface of a fin plate 44 serving as a flow rate detecting heat transfer member with an adhesive member 46 having good thermal conductivity, electrode pads of the flow rate detector 42 is connected to electrode terminals 48 through bonding wires 50, and the flow rate detector 42, bonding wires 50, a part of the fin plate 44 and the respective parts of the electrode terminals 48 are accommodated in a housing 52. The flow rate detector 42 is designed in the form of a chip in which a flow rate detecting thin-film temperature sensing element and a thin-film heating element are formed so as to be insulated to each other on a rectangular substrate of about 0.4 mm in thickness and about 2 mm in square formed of silicon, alumina or the like.

The fin plate 44 has an electroconductivity as well as good thermal conductivity and is made of Copper, Duralumin, Copper-tungsten alloy, etc.

As shown in FIG. 3, in the flow rate detecting unit 4, a part of the flow rate detecting fin plate 44 extends to form an electrode terminal 49. To the electrode terminal 49 is connected a connection line constituting a circuit for fluid discrimination. On the other hand, to the electrode terminals 48 are connected connection lines constituting a circuit for flow rate detection. Alternatively, instead of forming the electrode terminal 49 by a part of the flow rate detecting fin plate 44, the electrode terminal 49 may be made in the same manner as the electrode terminals 48 so that the electrode terminal 49 is connected to the flow rate detecting fin plate 44 through a bonding wire. In this case, a part of the fin plate 44 is made as a projecting area for use in wire bonding.

The fluid temperature detecting unit 6 has substantially the same constitution as the flow rate detecting unit 4 except that a fluid temperature detector is used instead of the flow rate detector 42. In the fluid temperature detecting unit 6, members corresponding to those of the flow rate detecting unit 4 are designated by the same reference numerals with a sign of prime ('). The fluid temperature detector has an analogous constitution to the flow rate detector 42 in which the thin-film heating element is removed.

End portions of the fin plates 44, 44' extend from the housings 52, 52' of the flow rate detecting unit 4 and the fluid temperature detecting unit 6 into the fluid flow passage 3 of the casing member 2. The fin plates 44, 44' extend to pass through the center of the cross section in the fluid flow passage 3 having substantially circular cross section. The fin plates 44, 44' are arranged along the flow direction of the fluid in the fluid flow passage 3, so that the heat exchange between the fluid and each of the flow rate detector 42 and fluid temperature detector 42' can be excellently performed without greatly disturbing the fluid flow.

Figure 4:
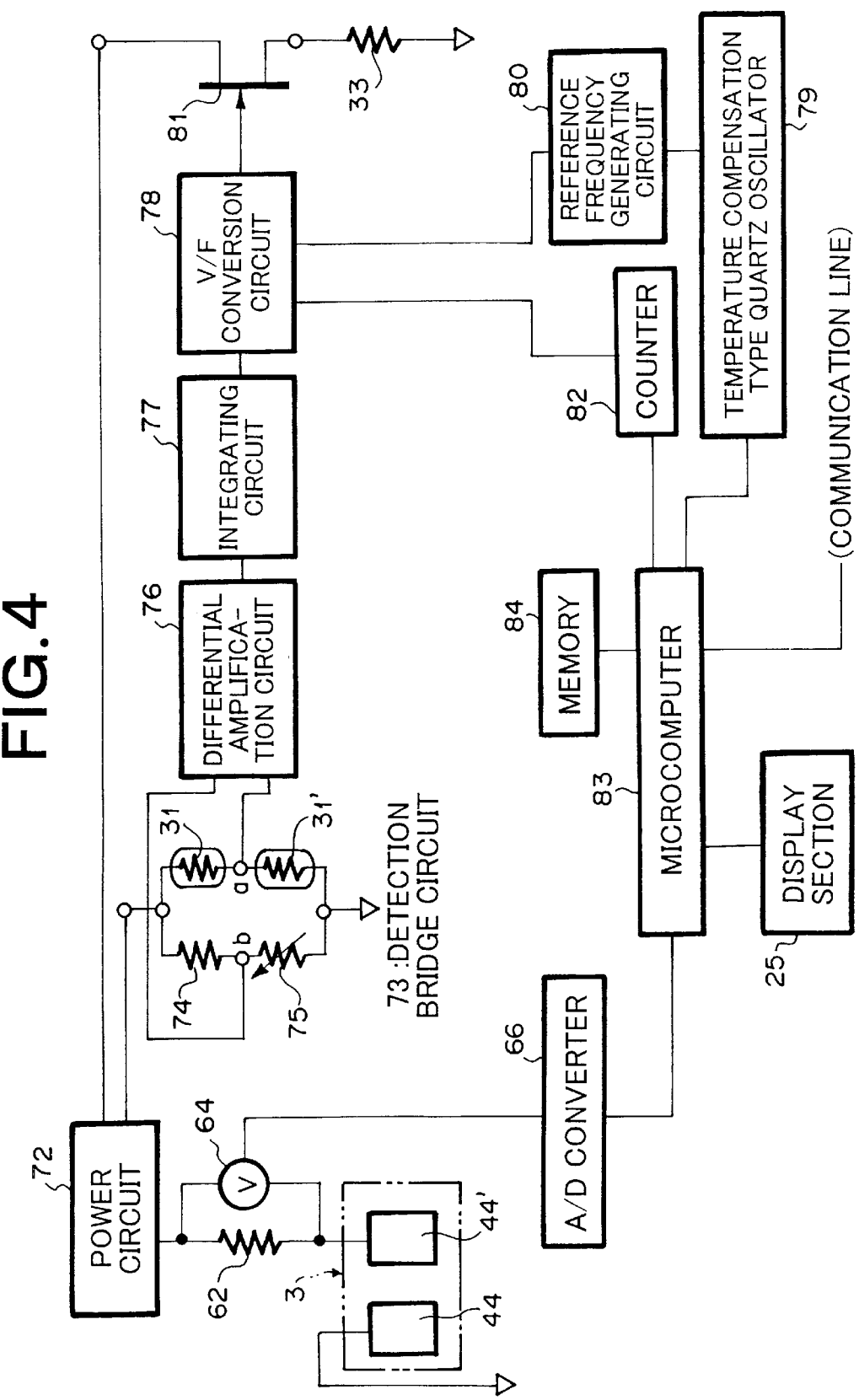
FIG. 4 is a circuit diagram of an embodiment of the flowmeter according to the present invention.

FIG. 4 is a circuit diagram of the above flowmeter.

Stabilized direct current supplied from a power circuit 72 is supplied to a bridge circuit (detection circuit) 73. The bridge circuit 73 contains a flow rate detecting temperature sensing element 31, a fluid temperature detecting temperature sensing element 31' for temperature compensation, a resistor 74 and a variable resistor 75. The potentials Va, Vb at the points a, b of the bridge circuit 73 is input to a differential amplification circuit 76 of variable amplification factor. The output of the differential amplification circuit 76 is input to an integrating circuit 77.

The output of the power circuit 72 is supplied to the thin-film heating element 33 through a field effect transistor 81 for controlling the current to be supplied to the thin-film heating element 33. That is, in the flow rate detector 42, the thin-film temperature sensing element 31 executes the temperature sensing (detecting) operation on the basis of the heating of the thin-film heating element 33 with being affected by the endothermic action of the fluid to be detected through the fin plate 44. As the result of the temperature sensing operation is achieved the difference between the potential Va at the point of a and the potential Vb at the point of b in the bridge circuit 73 shown in FIG. 4.

The value of (Va−Vb) is varied due to variation of the temperature of the flow rate detecting temperature sensing element 31 in accordance with the flow rate of the fluid. By setting the resistance value of the variable resistor 75 to an appropriate value in advance, the value (Va−Vb) may be set to zero when the flow rate of the fluid is equal to a desired value (reference value). At this reference flow rate value, the output value of the differential amplification circuit 76 is equal to zero, and thus the output value of the integrating circuit 77 is equal to a fixed value (the value corresponding to the reference flow rate value). The output of the integrating circuit 77 is adjusted with respect to the level so that the minimum value is 0V.

The output of the integrating circuit 77 is input to a V/F conversion circuit 78 to form a pulse signal having the frequency (for example, $5 \times 10^{-5}$ at maximum) corresponding to the voltage signal. The pulse signal has a fixed pulse width (time width) (for example, a desired value from 1 to 10 microseconds). For example, when the output of the integrating circuit 77 is equal to 1V, a pulse signal having a frequency of 0.5 kHz is output. When the output of the integrating circuit 77 is equal to 4V, a pulse signal having a frequency of 2 kHz is output.

The output of the V/F conversion circuit 78 is supplied to the gate of a transistor 81, and current is supplied to the thin-film heating element 33 through the transistor 81 having the gate to which is supplied the pulse signal. Accordingly, to the thin-film heating element 33 is supplied a divided voltage of the output voltage of the power circuit 72 through the transistor 81 in the form of a pulse at the frequency corresponding to the output value of the integrating circuit 77, so that the current flows through the thin-film heating element 33 intermittently to thereby heat the thin-film heating element 33. The frequency of the V/F conversion circuit 78 is set on the basis of high-precision clocks which are set on the basis of oscillation of a temperature compensation type quartz oscillator 79.

The pulse signal output from the V/F conversion circuit 78 is counted by a pulse counter 82. A microcomputer 83 converts the pulse count result (pulse frequency) to the corresponding flow rate (instantaneous flow rate) on the basis of a reference frequency generated in a reference frequency generating circuit 80, and integrates the flow rate thus achieved with respect to the time, thereby calculating an integrated flow rate.

Figure 5:
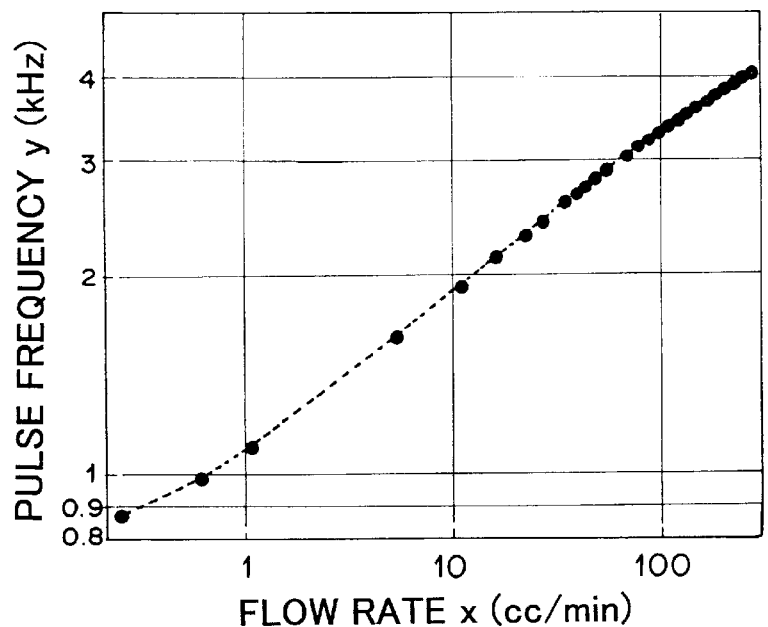
FIG. 5 is a diagram showing an example of calibration curve in the flowmeter of the present invention.

The conversion to the flow rate are performed by using a calibration curve for the required fluid to be subjected to flow rate detection stored in advance in a memory 84. FIG. 5 shows an example of the calibration curve. The calibration curve constitute a data table achieved by measuring the output (pulse frequency) of the pulse counter 82 every actual flow rate of the fluid. The microcomputer 83 determines as a detected flow rate value the flow rate value on the calibration curve corresponding to the pulse frequency achieved from the pulse counter 82 during the flow rate detection.

The instantaneous flow rate value and the integrated flow rate value thus achieved are displayed on a display section 25, and also transmitted to the outside through a communication line comprising a telephone line or other networks. Further, the data of the instantaneous flow rate and the integrated flow rate may be stored in the memory 84 if necessary.

When the flow rate of the fluid is increased/reduced, the output of the differential amplification circuit 76 is varied in polarity (varied in accordance with the sign (positive or negative) of the resistance-temperature characteristic of the flow rate detecting temperature sensing element 31) and magnitude in accordance with the value of (Va−Vb), and the output of the integrating circuit 77 is varied in accordance with this variation of the output of the differential amplification circuit 76. The variation rate of the output of the integrating circuit 77 can be adjusted by setting the amplification factor of the differential amplification circuit 76. The response characteristic of the control system is set by the integrating circuit 77 and the differential amplification circuit 76.

When the fluid flow rate is increased, the temperature of the flow rate detecting temperature sensing element 31 is reduced. Therefore, such an output (higher voltage value) that the heating value of the thin-film heating element 33 is increased (that is, the pulse frequency is increased) can be achieved from the integrating circuit 77, and the bridge circuit 73 is set to the equilibrium state at the time point when the output of the integrating circuit is equal to the voltage value corresponding to the fluid flow rate.

On the other hand, when the fluid flow rate is reduced, the temperature of the flow rate detecting temperature sensing element 31 is increased. Therefore, such an output (lower voltage value) that the heating value of the thin-film heating element 33 is reduced (that is, the pulse frequency is reduced) can be achieved from the integrating circuit 77, and the bridge circuit 73 is set to the equilibrium state at the time point when the output of the integrating circuit 77 is equal to the voltage corresponding to the fluid flow rate.

That is, in the control system of this embodiment, the frequency (corresponding to the heating value) of the pulse current to be supplied to the thin-film heating element 33 is set so that the bridge circuit 73 is set to the equilibrium state, and implementation of the equilibrium state (the response of the control system) as described above can be performed within 0.1 second, for example.

Furthermore, the output of the power circuit 72 is supplied to the fluid temperature detecting fin plate 44' via a resistor 62 of high resistance value (for example, about 10 kΩ) and the above-mentioned electrode terminal 49', and the flow rate detecting fin plate 44 is grounded via the above-mentioned electrode terminal 49. A voltmeter 64 is connected to both the ends of the resistor 62. A voltage value detected by the voltmeter 64 corresponds to a current value flowing between the fin plates 44, 44' through the fluid introduced into the fluid flow passage 3, and to a resistance value of the fluid existing between the fin plates 44, 44'. These members constitute a circuit for detecting or determining the conductivity between the flow rate detecting fin plate 44 and the fluid temperature detecting fin plate 44'.

The output of the voltmeter 64 is input to the microcomputer 83 via an A/D converter 66. In the memory 84 is stored data of the range (hereinafter referred to as "specific range") for the output value of the voltmeter 64 to be detected with respect to the required fluid by the circuit for detecting or determining the conductivity. The specific range is suitably set in advance by introducing the required fluid to be subjected to flow rate detection to detect the output value of the voltmeter 64 of the circuit for detecting or determining the conductivity, and by taking the detection error range into consideration. For example, in case of a physiological saline solution used as the required fluid, the specific range is set to 3.2 to 3.6V in the circuit for detecting or determining the conductivity. In such a circuit for detecting or determining the conductivity, the output value of the voltmeter 64 is 0.8 to 1.2V for tap water, and 0.05V or less for alcohol or acetone. Therefore, if these non-required fluid is erroneously introduced into the fluid flow passage, it can be possible to discriminate the non-required fluid from the required fluid.

Figure 6:
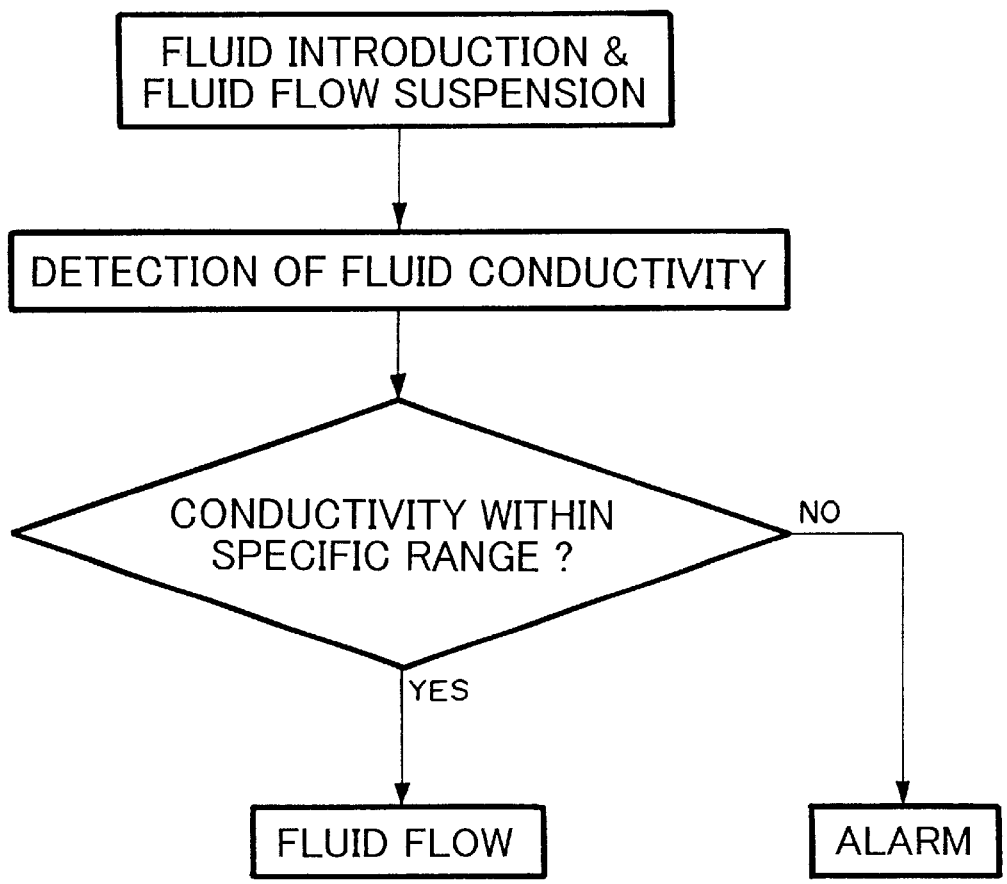
FIG. 6 is a flowchart of fluid discrimination.

In the embodiment of the present invention, first, the fluid is introduced into the fluid flow passage 3, and the degree of conductivity (that is, voltage value of the output of the voltmeter 64) of the fluid in the fluid flow passage 3 without allowing the fluid flow prior to the flow rate detection of the fluid. The microcomputer 83 makes judgement as to whether the voltage value which is input from the A/D converter 66 and signifies the degree of the conductivity is a value within the specific range stored in the memory 84 or not. In case that the voltage value of the output of the voltmeter 64 is determined as being within the specific range, the fluid introduced into the fluid flow passage is judged as the required fluid and subsequently the fluid is fed from the fluid source into the fluid flow passage to allow the fluid flow through the fluid flow passage 3 while detecting the fluid flow rate as described in the above. On the other hand, in case that the voltage value of the output of the voltmeter 64 is determined as being without the specific range, the fluid is judged as the non-required fluid, so that the fluid is no more fed from the fluid source into the fluid flow passage and an alarm is given which the fluid introduced into the fluid flow passage is not the required fluid. Such an alarm can be effected by an alarm signal indicated on the display section 25 or by an alarm sound generated by suitable alarm means (not shown). FIG. 6 is a flowchart of such a fluid discrimination.

Accordingly, according to the flowmeter of this embodiment, the above fluid discrimination is carried out every time when the liquid source is changed to a fresh one, and thus it can be avoided to erroneously allow the flow of the fluid having the conductivity different from that of the required fluid to be subjected to the flow rate detection, that is, the erroneous flow of the non-required fluid can be surely prevented.

According to the above-described embodiment, the pulse signal generated in the V/F conversion circuit 78 is used to measure or detect the flow rate, and it is easy to sufficiently reduce the error of the pulse signal due to the temperature variation. Therefore, the errors of the flow rate value and the integrated flow rate value achieved on the basis of the pulse frequency can be reduced. Further, according to this embodiment, the control of the current supply to the thin-film heating element 33 is performed by ON/OFF based on the pulse signal generated in the V/F conversion circuit 78. Therefore, the probability that a control error due to the temperature variation occurs is extremely small.

Further, this embodiment uses a minute chip containing the thin-film heating element and the thin-film temperature sensing element as the flow rate detector, so that the high-speed response as described above can be implemented and the precision of the flow rate measurement is excellent.

Still further, according to this embodiment, irrespective of the flow rate of the fluid to be subjected to the flow rate detection, the temperature of the flow rate detecting temperature detector 31 existing in the vicinity of the thin-film heating element 33 is set to a substantially constant value, so that deterioration of the flow rate detecting unit with time can be suppressed and occurrence of ignition explosion of combustible fluid to be subjected to the flow rate detection can be prevented.

INDUSTRIAL APPLICABILITY

As described above, according to the flowmeter of the present invention, the fluid discrimination is effected by determining the conductivity of the fluid existing between the flow rate detecting electroconductive heat transfer member and the fluid temperature detecting electroconductive heat transfer member which are also used in the flow rate detection, and therefore it can be avoided with simple constitution to erroneously allow the flow of the fluid having the conductivity different from that of the required fluid to be subjected to the flow rate detection.

What is claimed is:

1. A thermal flowmeter, comprising:

a flow rate detecting unit comprising a heating element, a flow rate detecting temperature sensing element and a flow rate detecting electroconductive heat transfer member extending into a fluid flow passage, which are disposed so as to enable heat transfer therebetween, said flow rate detecting temperature sensing element varying in electrical characteristic value in accordance with the flow of the fluid in the fluid flow passage through heat exchange with the fluid in the fluid flow passage which is carried out through the flow rate detecting electroconductive heat transfer member; and a fluid temperature detecting unit comprising a fluid temperature detecting temperature sensing element and a fluid temperature detecting electroconductive heat transfer member extending into said fluid flow passage, which are disposed so as to enable heat transfer therebetween, said fluid temperature detecting temperature sensing element varying in electrical characteristic value in accordance with the temperature of the fluid through the heat exchange with the fluid in the fluid flow passage, wherein the flow rate of the fluid is detected on the basis of the electrical characteristic value of the flow rate detecting temperature sensing element and the electrical characteristic value of the fluid temperature detecting temperature sensing element, and wherein said thermal flowmeter is adapted to determine a conductivity of the fluid between the flow rate detecting electroconductive heat transfer member and the fluid temperature detecting electroconductive heat transfer member to thereby effect a fluid discrimination.

2. The thermal flowmeter as claimed in claim 1, wherein the fluid discrimination is effected by judging the fluid as a required one in case that when a detected value of current flowing between the flow rate detecting electroconductive heat transfer member and the fluid temperature detecting electroconductive heat transfer member therethrough falls within a predetermined range for the required fluid, while judging the fluid as not the required one in case that the detected value of current falls without the predetermined range for the required fluid.

3. The thermal flowmeter as claimed in claim 1, wherein the flow rate of the fluid is detected on the basis of an output of a detection circuit containing said flow rate detecting temperature sensing element and said fluid temperature detecting temperature sensing element and a calibration curve.

4. The thermal flowmeter as claimed in claim 1, wherein a portion of said flow rate detecting electroconductive heat transfer member comprises a first electrode terminal for a circuit for determining the conductivity, and a portion of said fluid temperature detecting electroconductive heat transfer member comprises a second electrode terminal for said circuit for determining the conductivity.

5. The thermal flowmeter as claimed in claim 4, wherein said flow rate detecting unit further comprises a first housing comprising said heating element and said flow rate detecting temperature sensing element, wherein said first electrode terminal extends from said first housing; and wherein said fluid temperature detecting unit comprises a second housing comprising said fluid temperature detecting temperature sensing element, wherein said second electrode terminal extends from said second housing.

6. The thermal flowmeter as claimed in claim 1, further comprising a circuit for determining the conductivity comprising a power circuit for applying a voltage between said flow rate detecting electroconductive heat transfer member and said fluid temperature detecting electroconductive heat transfer member, and a detector for detecting a resistance value of the fluid between said flow rate detecting electroconductive heat transfer member and said fluid temperature detecting electroconductive heat transfer member.

7. The thermal flowmeter as claim in claim 6, wherein said detector comprises a resistor having ends through which the voltage is applied between said flow rate detecting electroconductive heat transfer member and said fluid temperature detecting electroconductive heat transfers member, and a voltmeter for detecting a voltage value between the ends of said resistor.

* * * * *

UNITED STATES PATENT AND TRADEMARK OFFICE
CERTIFICATE OF CORRECTION

PATENT NO. : 6,681,624 B2
DATED : January 27, 2004
INVENTOR(S) : Shinya Furuki et al.

It is certified that error appears in the above-identified patent and that said Letters Patent is hereby corrected as shown below:

<u>Title page, Item [54], and Column 1, line 2,</u>
Title, change "DESCRIMINANT FUNCTION" to -- DISCRIMINANT FUNCTION--.

Signed and Sealed this

Fourth Day of May, 2004

JON W. DUDAS
*Acting Director of the United States Patent and Trademark Office*